United States Patent [19]

Pugach et al.

[11] Patent Number: 5,502,240

[45] Date of Patent: Mar. 26, 1996

[54] ESTERIFICATION PROCESS USING A TITAMIUM ZEOLITE CATALYST

[75] Inventors: Joseph Pugach, Monroeville Borough; Thomas W. Smeal, Municipality of Murrysville; Howard S. Karp, Monroeville Borough, all of Pa.

[73] Assignee: Aristech Chemical Corporation, Pittsburgh, Pa.

[21] Appl. No.: 488,561

[22] Filed: Jun. 9, 1995

[51] Int. Cl.$^6$ ................................................ C07C 64/08
[52] U.S. Cl. ............................................ 560/99; 560/204
[58] Field of Search ........................................ 560/99, 204

[56] References Cited

U.S. PATENT DOCUMENTS

| | | | |
|---|---|---|---|
| 2,928,853 | 3/1960 | Bond, Jr. | 260/410.9 |
| 3,056,817 | 10/1962 | Werber et al. | 260/404.08 |
| 4,032,550 | 6/1977 | White et al. | 260/410.6 |
| 5,183,930 | 2/1993 | Venter et al. | 560/217 |
| 5,401,486 | 3/1995 | Mueller et al. | 423/705 |

*Primary Examiner*—José G. Dees
*Assistant Examiner*—Samuel Barts
*Attorney, Agent, or Firm*—William L. Krayer; Robert R. Gavlik

[57] ABSTRACT

A liquid phase esterification process is described wherein the esterification catalyst is a titanium zeolite.

10 Claims, No Drawings

ण्‍5,502,240

ESTERIFICATION PROCESS USING A TITAMIUM ZEOLITE CATALYST

TECHNICAL FIELD

This invention relates to the use of zeolites as heterogeneous liquid phase catalysts in esterification reactions. More specifically it relates to the use of titanium containing zeolites in which the aluminum content is negligible. These highly crystalline catalysts can be easily removed from the final reaction mixture and recycled to a fresh reaction.

BACKGROUND OF THE INVENTION

Esterification processes that manufacture plasticizers are typically run in the liquid phase using homogeneous catalysts. These catalysts must be removed from the plasticizer effluent and this entails extra processing steps as well as creating waste water. A highly crystalline heterogeneous catalyst on the other hand, may be easily recovered by filtration or any other suitable means and recycled to the next reaction batch. This has advantages in that extra processing steps are eliminated, waste water is not generated, and spent catalyst disposal is minimized.

Amorphous titanium containing heterogeneous liquid phase catalysts are known in the art, but results are typically poor. The difference between a zeolite and the amorphous materials is that the Ti is incorporated into the lattice framework of the crystal; it is an inherent part of the molecular structure. In contrast, the amorphous catalyst consists mainly of $TiO_2$ adsorbed or coated on the surface of a carrier. The Ti is not an integral part of the carrier structure.

U.S. Pat. No. 4,032,550 discloses the preparation and use of titanium supported on monmorillonite clay as well as alumina and silica as catalysts for esterification and transesterification reactions. The method of preparation is complicated and typically Ti concentrations as high as 35% are disclosed. The Ti level is much higher than in the Ti zeolites.

U.S. Pat. No. 5,183,930 discloses the preparation of amorphous $TiO_2/SiO_2$ and $TiO_2/Al_2O_3$ catalysts for transesterification reactions. Amorphous $Ti(OH)_x$ is formed via the controlled hydrolysis of a Ti alkoxide, and is then put on the carrier. However, this material is not used as a direct esterification catalyst.

U.S. Pat. No. 3,056,817 discloses the use of hydrous titania gel. The gel is distinguished from dry titania, and is said to have no activity as an esterification catalyst. The titania gel is not an effective catalyst at reaction temperatures above 150° C.

U.S. Pat. No. 2,928,853 discloses direct esterification catalyzed by $TiSO_4$ on a carrier such as a clay. Again, this is an amorphous material and suffers from the disadvantage of sulfur contamination.

SUMMARY OF THE INVENTION

The present invention is drawn to a method of making an esterification product using a heterogeneous titanium zeolite catalyst. This catalyst is useful for direct esterifications such as plasticizer manufacturing. An example of such a plasticizer is the di-2-ethyl hexyl ester of phthalic acid. Other acids within the scope of this invention are adipic acid, trimelitic acid and in general, any acid whose ester can find use as a plasticizer. Similarly, alcohols within the scope of this invention include normal linear alcohols having from four to fifteen carbon atoms and mixtures of these. Branched alcohols containing four to fifteen carbon atoms and their mixtures are also included. In general, any alcohol known in the art to find utility in plasticizer manufacture is included.

This catalyst enhances the performance of direct esterification reactions such as plasticizer manufacture processes. The use of such a catalyst eliminates the waste water generated in other esterification processes, and is therefore, an environmentally efficient process. The expense and contamination associated with waste water is completely eliminated. The catalyst can also be recovered via filtration or any other convenient means known in the art, and can be recycled a multiple number of times. This leads to a considerable saving in overall catalyst cost.

The titanium catalyst can be made by known processes in the art (see examples one and two, infra.). The basic procedure for the esterification is to react one mole of a carboxylic acid with 1.0–2.0 moles per carboxylic acid group and 0.5–50 g of the titanium zeolite catalyst at reaction temperatures of 180° C.–280° C. and removing the water of reaction until the acid number is <0.1 (i.e. mg. of KOH/g of esterified product). The reaction mixture is cooled, excess alcohol is removed under vacuum and the esterified product is recovered after filtration through a bed of fuller's earth. The catalyst can also be recovered by filtration or any other suitable means before the alcohol is removed and recycled to a fresh reaction. In the case above, the alcohol would be removed under vacuum after the catalyst removal step.

DETAILED DESCRIPTION OF THE INVENTION

In applicants' preferred embodiment, 1.0 moles of phthalic anhydride, about 2.1–2.5 moles of 2-ethylhexanol and about 5.0–20.0 g of the catalyst as reported in Example 1 are added to a reaction vessel. The vessel is heated to a temperature of about 210°–230° C. The reaction is allowed to proceed until the acid number of the mixture drops to <0.1. The reaction mixture is then cooled to about 90° C., and then filtered to recover the catalyst. Excess alcohol is removed under vacuum, and the di-2-ethylhexyl phthalate product is then filtered through fuller's earth to polish it.

Applicants' invention is illustrated by, but not limited to the following examples:

Preparation I of the Titanium Zeolite Two solutions were prepared as follows:

Solution A: 455.6 g of sodium silicate was dissolved in 478.7 g of deionized water at room temperature.

Solution B: To 637.5 g of deionized water was added 58.4 g of tetra-n-propyl ammonium bromide, 44.3 g $MgCl_2$, 170.9 g NaCl and 24.4 g of Tyzor LA. The mixture was stirred at room temperature until a clear solution was obtained. Tyzor LA is a lactic acid chelate ammonium salt of titanium, and is manufactured by dupont.

The two solutions were then added to one another with stirring at room temperature at such a rate that in one hour addition of both solutions was complete. The mixture was then placed into a Teflon container which in turn was put into a 2 L Parr autoclave. The mixture was heated between 160°–170° C. for three days after which the autoclave was allowed to cool. The granular precipitate which formed was filtered and the filter cake was slurried with one L of deionized water at 80° C. for one hour, and filtered. The wet cake was dried overnight at 130° C.

The dried powder was slurried in 2 L of water, 100 g of $NH_4CL$ was added, an additional 1700 ml of deionized water was added and the mixture was heated with stirring at 70°–80° C. for 1.0 hours. The mixture was filtered and the solids obtained treated as above two more times. The final solid was dried at 130° C. overnight, ground in a mortar and pestle and transferred to a porcelain dish. The dish was placed in an electric oven, and the temperature raised to 500° C. at a rate of 10°/minute. The solid was calcined at 500° C. for a total of ten hours to give the hydrogen form of the Ti zeolite.

Preparation II of the Titanium Zeolite

This procedure is essentially the same as in Example 1 of U.S. Pat. No. 4,410,501.

To a three-necked flask equipped with a mechanical stirrer, a dropping funnel and a Vigreaux distillation column was added 250 g of tetraethylortho silicate under an Argon atmosphere. 10 g of tetra-isopropyl titanate was then added via a pipette, followed by 400 g of an aqueous 25 wt. % solution off tetra-n-propylammonium hydroxide. The mixture was stirred for 1.0 hours, and the temperature then raised. The alcohols were removed by distillation over a 5.0 hour period. After cooling, enough deionized water was added to bring the volume of the solution up to 800 ml, and this mixture was then transferred to a Teflon container which in turn was put into a 2 L Parr autoclave. The mixture was then heated to 175° C. and kept at that temperature under autogenous pressure for seven days. The solid obtained after cooling was filtered and dried at 130° C. overnight. The dried powdery solid was placed in a porcelain crucible and calcined at 550° C. for six hours to give the hydrogen form of the Ti zeolite.

EXAMPLE 1

A one-liter Morton flask with 4 necks was fitted with a stirrer for vigorous agitation, a sparge for inert gas, a closed sample tube, a Friedrichs condenser and a Dean-Stark trap for separation of reaction water. Heat was supplied by electric heating mantles controlled by a thermocouple in the flask and an Omega temperature controller. To this flask was charged 148.1 grams (g) of phthalic anhydride [1.0 mole], 325.0 g of 2-ethylhexanol [2.5 moles] and 12.5 g of the titanium zeolite of Preparation II [2.5%] as the catalyst. Heatup commenced, with the first drop of water collected at a temperature of 176° C. in the flask and the top reaction temperature of about 230° C. was reached about 2.25 hours later. Four hours after the first water the acid number was 2.5 and 3.5 hours later it was 0.043 and the reaction was ended. The batch was cooled to 95° C. and filtered through 2 layers of Whatman #41 filter paper to recover the catalyst. The excess alcohol was removed with a wiped-film evaporator and the di-2 ethylhexyl phthalate (DOP) product was filtered through a bed of fuller's earth to polish it. This DOP had an acidity of 0,001% and an APHA color of 28 with good clarity. After exposure to 220° C. for 2 hours, the color and clarity had not changed.

Comparative Example 1

Example 1 was repeated without a catalyst. Four hours after the first water the acid number was about 12 and 7 hours later it was still about 4. The experiment was aborted at this point as this result is unsatisfactory.

EXAMPLE 2

Example 1 was repeated with 10.0 g (2.0%) of the titanium zeolite of Preparation II as the catalyst. Four hours after the first water the acid number was 3.7 and 3.5 hours later it was 0.062. Catalyst recovery and product purification proceeded in a fashion that was very similar to Example 1 except that the APHA color was 20 before heating and 23 after.

EXAMPLE 3

Example 1 was repeated with 5.0 g (1.0%) of the titanium zeolite of Preparation II as the catalyst. Four hours after first water the acid number was 7.2 and 8.75 hours later it was 0.071. Catalyst recovery and product purification proceeded in a fashion that was very similar to Example 1 except that the APHA color was 18 before and after heating.

EXAMPLE 4

Example 1 was repeated with 9.1 g (1.8%) of the titanium zeolite catalyst of Preparation II that was recovered after use in Example 1 as the catalyst. Four hours after first water the acid number was <3 and 3 hours later it was 0.078. Catalyst recovery and product purification proceeded in a fashion that was very similar to Example 1 except that the APHA color was 18 before heating and 23 after.

EXAMPLE 5

Example 1 was repeated with 15.0 (3.0%) of the titanium zeolite of Preparation I as the catalyst. 2.25 hours after first water the acid number was 1.9 and 4 hours later it was about 0.05. The catalyst was recovered and the product was not purified; however, there was no indication that the product quality was not good.

EXAMPLE 6

Example 1 was repeated with 17.7 g (3.5%) of the titanium zeolite catalyst of Preparation I that was recovered after use as the catalyst in Example 5 and another similar experiment. 2.25 hours after first water the acid number was 4.9 and 50 minutes later had dropped to 0.83. 6.5 hours after first water the acid number was 0.047. Catalyst recovery and product purification proceeded in a fashion that was very similar to Example 1 except that the APHA color was 15 before heating and 17 after.

EXAMPLE 7

Example 1 was repeated with 25.0 g (5.0%) of the titanium zeolite of Preparation I as the catalyst. Two hours after first water the acid number was 1.8 and 45 minutes later it was 0.078. The catalyst was recovered and the product was purified with the results of an acidity of 0.003% and an APHA color (13) that was better than Example 1 but which darkened to 55 and became slightly hazy upon heating to 220° C. for 2 hours.

EXAMPLE 8

Example 1 was repeated with 12.0 (2.4%) of the titanium zeolite of Preparation I as the catalyst. Three hours after first water the acid number was 1.8 and 7.25 hours later it was 0.089. The catalyst was recovered but the product was not purified.

Comparative Example 2

Example 1 was repeated with 15.0 g (3.0%) of ZSM-5 zeolite as the catalyst. ZSM-5 has the same structure as the Ti zeolite except the Ti has been replaced by Al. Five hours after first water the acid number was 21.2, an excessive amount of water had been collected (an indication of alcohol dehydration or some other undesirable reaction) and the contents of the flask were highly discolored. The experiment was aborted at this point.

Comparative Example 3

Example 1 was repeated with 15.0 g (3.0%) of Engelhard Pentasil L-3919 zeolite as the catalyst. Six hours after first water the acid number was 9.6, a slightly excessive amount of water had been collected and the contents of the flask were highly discolored. The experiment was aborted at this point.

I claim:

1. A process of preparing an ester, comprising the steps of:
   (a) making a reaction mixture comprising, an alcohol, a carboxylic acid, and a heterogeneous titanium zeolite catalyst;
   (b) heating said reaction mixture; and
   (c) allowing said reaction mixture to react, wherein water is removed to drive the formation of said ester.

2. The process of claim 1 further comprising the step of recycling said catalyst to another reaction.

3. The process of claim 1 wherein the reaction mixture is heated to about 180° to about 280° C.

4. The process of claim 1 wherein the molar ratio of alcohol to carboxylic acid group is about 1.0 to about 4.0.

5. The process of claim 1 wherein said catalyst is up to about 10 wt. % of the initial charge.

6. The process of claim 1 wherein said alcohol is 2-ethylhexanol.

7. The process of claim 1 wherein said carboxylic acid is phthalic acid.

8. The process of claim 1 wherein the reaction temperature is about 210° to about 230° C.

9. A process of preparing an ester, comprising the steps of:
   (a) making a reaction mixture comprising, an alcohol, a carboxylic acid, and a heterogeneous titanium zeolite catalyst;
   (b) heating said reaction mixture;
   (c) allowing said reaction mixture to react, wherein water is removed to drive the formation of said ester;
   (d) removing the catalyst;
   (e) recovering excess alcohol; and
   (f) recovering said ester.

10. The process of claim 9 wherein said ester product is filtered through a bed of fuller's earth.

* * * * *